United States Patent
Paul

(10) Patent No.: US 11,219,589 B2
(45) Date of Patent: Jan. 11, 2022

(54) METHOD OF STRENGTHENING OXIDATIVELY-TREATED HAIR

(71) Applicant: Conopeo, Inc., Englewood Cliffs, NJ (US)

(72) Inventor: Prem Kumar Cheyalazhagan Paul, Wirral (GB)

(73) Assignee: CONOPCO, INC, Englewood Cliffs, NJ (US)

( * ) Notice: Subject to any disclaimer, the term of this patent is extended or adjusted under 35 U.S.C. 154(b) by 199 days.

(21) Appl. No.: 16/482,134

(22) PCT Filed: Feb. 5, 2018

(86) PCT No.: PCT/EP2018/052826
§ 371 (c)(1),
(2) Date: Jul. 30, 2019

(87) PCT Pub. No.: WO2018/146051
PCT Pub. Date: Aug. 16, 2018

(65) Prior Publication Data
US 2021/0038489 A1     Feb. 11, 2021

(30) Foreign Application Priority Data
Feb. 13, 2017   (EP) ..................... 17155868

(51) Int. Cl.
*A61K 8/44*   (2006.01)
*A61Q 5/00*   (2006.01)

(52) U.S. Cl.
CPC ................ *A61K 8/44* (2013.01); *A61Q 5/002* (2013.01); *A61K 2800/80* (2013.01)

(58) Field of Classification Search
CPC ..................................................... A61K 8/44
See application file for complete search history.

(56) References Cited

U.S. PATENT DOCUMENTS

| | | | |
|---|---|---|---|
| 6,159,485 | A | 12/2000 | Yu et al. |
| 6,808,716 | B2 | 10/2004 | Yu et al. |
| 2004/0258652 | A1 | 12/2004 | Pascaly et al. |
| 2010/0061953 | A1 | 3/2010 | Luengo et al. |
| 2010/0080761 | A1* | 4/2010 | Herrmann ............ A61K 8/9789 424/45 |
| 2017/0079897 | A1 | 3/2017 | Minus |

FOREIGN PATENT DOCUMENTS

| | | |
|---|---|---|
| CA | 2023090 | 2/1991 |
| CA | 2144912 | 9/1995 |
| CN | 1336817 | 2/2002 |
| EP | 0422765 | 4/1991 |
| EP | 1493423 | 6/2006 |
| FR | 2912650 | 8/2008 |
| KR | 20150062590 | 6/2015 |
| WO | WO0040217 | 7/2000 |

OTHER PUBLICATIONS

Kumar et al. (Thermochimica Acta 583 (2014) 49-58). (Year: 2014).*
Marsh et al. (J. Cosmet. Sci., 2009, 60, 205-215). (Year: 2009).*
IPRP1 in PCTEP2018052835; dated Aug. 13, 2019; World Intellectual Property Org. (WIPO).
Search Report and Written Opinion in EP17155868; dated May 12, 2017; European Patent Office (EPO).
IPRP1 in PCTEP2018052826; dated Aug. 13, 2019; World Intellectual Property Org. (WIPO).
Co-pending Application, Paul et al., dated Jul. 29, 2019, U.S. Appl. No. 16/481,606.
N-alpha-Acetyl-L-lysine Metabocard (HMDB0000446); Human Metabolome Database; 2005; pp. 1-7, Retrieved from the Internet:<https://hmdb.ca/metabolites/HMDB0000446>.
Search Report and Written Opinion in PCTEP2018052826; dated Apr. 13, 2018.
Amorepacific Corp; Clarivate Analytics; Database WPI Thomson Scientific; pp. 1-3 XP002769643 2017.
Search Report and Written Opinion in PCTEP2018052835; dated Apr. 9, 2018.
Search Report and Written Opinion in EP17155882 ; dated May 12, 2017.
Shi Changqing et al.; Synthesis of two N-protected lysines; Natural Science Edition; Jan. 31, 2004; PP60-62; Original document only; vol. 20 No. 1; Journal of Soochow University; China.
Shi Changqing et al.; Synthesis of two N-protected lysines; Natural Science Edition; Jan. 31, 2004; PP60-62; English translation; vol. 20 No. 1; Journal of Soochow University; China.

* cited by examiner

*Primary Examiner* — Benjamin J Packard
(74) *Attorney, Agent, or Firm* — Krista A. Kostiew

(57) ABSTRACT

The invention provides a method of strengthening the fibres of oxidatively-treated hair, the method comprising the sequential steps of: (i) washing the oxidatively-treated hair; (ii) soaking the washed hair in an aqueous treatment composition, and (iii) drying the soaked hair; characterised in that the aqueous treatment composition comprises at least 1% N-acetyl glycine (by weight based on the total weight of the composition).15 The invention also provides the use of an aqueous treatment composition comprising at least 1% N-acetyl glycine (by weight based on the total weight of the composition), for the enhanced strengthening of oxidatively-treated hair fibres relative to virgin hair fibres.

5 Claims, No Drawings

METHOD OF STRENGTHENING OXIDATIVELY-TREATED HAIR

CROSS-REFERENCE TO RELATED APPLICATIONS

This application is a U.S. national phase application under 35 U.S.C. § 371 of International Application No. PCT/EP2018/052826, filed on Feb. 5, 2018, which claims priority to EP Patent Application No. 17155868.7, filed Feb. 13, 2017, the entire disclosures of which are incorporated herein by reference in their entireties, for any and all purposes.

FIELD OF THE INVENTION

This invention relates to a method of strengthening the fibres of oxidatively-treated hair.

BACKGROUND OF THE INVENTION

The purpose of bleaching is to eliminate or lighten the natural hair colour by the reaction of an oxidizing agent with the melanin pigment. Examples of oxidizing agents that can be used are hydrogen peroxide, potassium, sodium or ammonium salts of perborate, percarbonate, persulfate and percarbamide, and mixtures thereof. Bleaches are also used during oxidative dyeing treatments. Oxidative (or "permanent") dye compositions comprise "precursor dyes" which are small molecules capable of diffusing into the hair. These molecules mainly belong to three classes of aromatic compounds: diamines, aminophenols and phenols. They are sufficiently small to diffuse in the hair shaft where, once activated by an oxidizing agent such as hydrogen peroxide, they further react with other precursors to form larger coloured complexes.

Oxidative treatments of hair are very popular with consumers since they provide good results which are relatively unaffected by light, shampooing and perspiration. However, the process is not without drawbacks. Repeated oxidative treatments over prolonged periods may damage or weaken hair, making it prone to breakage and reduced lustre.

Film-forming polymers are often used in treatments for damaged hair because they alter hair surface properties, imparting smoothing and gliding effects and shine, and have a significant impact on the macroscopic behavior of the hair array. However, film-forming polymers are by nature designed to provide hair fibres with a hydrophobic coating that may slow or prevent the penetration of actives. Therefore, such treatments may not provide intrinsic benefits to the fibre such as strengthening and repair. The polymers themselves may also deposit less effectively on damaged hair compared to virgin hair.

The present invention addresses this problem.

SUMMARY OF THE INVENTION

The present invention provides a method of strengthening the fibres of oxidatively-treated hair, the method comprising the sequential steps of:
(i) washing the oxidatively-treated hair;
(ii) soaking the washed hair in an aqueous treatment composition, and
(iii) drying the soaked hair;
characterised in that the aqueous treatment composition comprises at least 1% N-acetyl glycine (by weight based on the total weight of the composition).

The invention also provides the use of an aqueous treatment composition comprising at least 1% N-acetyl glycine (by weight based on the total weight of the composition), for the enhanced strengthening of oxidatively-treated hair fibres relative to virgin hair fibres.

DETAILED DESCRIPTION AND PREFERRED EMBODIMENTS

All molecular weights as used herein are weight average molecular weights, unless otherwise specified.

The aqueous treatment composition for use in step (ii) of the method of the invention will typically comprise an aqueous continuous phase.

By "aqueous continuous phase" is meant a continuous phase which has water as its basis. Accordingly, the aqueous treatment composition will generally comprise at least 60%, preferably at least 70% and more preferably at least 80% water (by weight based on the total weight of the composition). Preferably, the composition comprises no more than 99% and more preferably no more than 98% water (by weight based on the total weight of the composition). Other organic solvents may also be present, such as lower alkyl alcohols and polyhydric alcohols. Examples of lower alkyl alcohols include $C_1$ to $C_6$ monohydric alcohols such as ethanol and isopropanol. Examples of polyhydric alcohols include propylene glycol, hexylene glycol, glycerin, and propanediol. Mixtures of any of the above described organic solvents may also be used.

The aqueous treatment composition for use in step (ii) of the method of the invention comprises at least 1% N-acetyl glycine (by weight based on the total weight of the composition).

The N-acetyl glycine may be used in the free acid form or in the form of salts such as the sodium, potassium, and ammonium salts, or the lower alkanolamine salts (such as mono-, di- and triethanolamine salts and mono-, di- and triisopropanolamine salts). Mixtures of any of the above-described forms may also be suitable.

Preferably the N-acetyl glycine is used in the free acid form, and at a level ranging from 1 to 6%, more preferably from 1 to 3% and most preferably from 1.5 to 2.5% (by weight based on the total weight of the composition).

An aqueous treatment composition for use in step (ii) of the method of the invention may suitably include a conditioning gel phase, which may be generally characterized as a gel (Lβ) surfactant mesophase consisting of surfactant bilayers. Such a conditioning gel phase may be formed from a cationic surfactant, a high melting point fatty alcohol and an aqueous carrier. Typically, these components are heated to form a mixture, which is cooled under shear to room temperature. The mixture undergoes a number of phase transitions during cooling, normally resulting in a gel ($L_β$) surfactant mesophase consisting of surfactant bilayers.

Examples of suitable cationic surfactants which are useful for forming the conditioning gel phase include quaternary ammonium cationic surfactants corresponding to the following general formula:

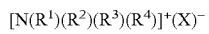

in which $R^1$, $R^2$, $R^3$, and $R^4$ are each independently selected from (a) an aliphatic group of from 1 to 22 carbon atoms, or (b) an aromatic, alkoxy, polyoxyalkylene, alkylamido, hydroxyalkyl, aryl or alkylaryl group having up to 22 carbon atoms; and X is a salt-forming anion such as those selected from halide, (e.g. chloride, bromide), acetate, citrate, lactate, glycolate, phosphate nitrate, sulphate, and alkylsulphate radicals.

The aliphatic groups can contain, in addition to carbon and hydrogen atoms, ether linkages, and other groups such as amino groups. The longer chain aliphatic groups, e.g., those of about 12 carbons, or higher, can be saturated or unsaturated. Specific examples of such quaternary ammonium cationic surfactants of the above general formula are cetyltrimethylammonium chloride, behenyltrimethylammonium chloride (BTAC), cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, dipalmitoylethyldimethylammonium chloride, PEG-2 oleylammonium chloride and salts of these, where the chloride is replaced by other halide (e.g., bromide), acetate, citrate, lactate, glycolate, phosphate nitrate, sulphate, or alkylsulphate.

In a preferred class of cationic surfactant of the above general formula, $R^1$ is a $C_{16}$ to $C_{22}$ saturated or unsaturated, preferably saturated, alkyl chain and $R^2$, $R^3$ and $R^4$ are each independently selected from $CH_3$ and $CH_2CH_2OH$, preferably $CH_3$.

Specific examples of such preferred quaternary ammonium cationic surfactants for use in forming the conditioning gel phase are cetyltrimethylammonium chloride (CTAC), behenyltrimethylammonium chloride (BTAC) and mixtures thereof.

Mixtures of any of the above-described cationic surfactants may also be suitable.

The level of cationic surfactant suitably ranges from 0.1 to 10%, preferably from 0.2 to 5% and more preferably from 0.25 to 4% (by weight based on the total weight of the composition).

By "high melting point" in the context of this invention is generally meant a melting point of 25° C. or higher. Generally, the melting point ranges from 25° C. up to 90° C., preferably from 40° C. up to 70° C. and more preferably from 50° C. up to about 65° C.

The high melting point fatty alcohol can be used as a single compound or as a blend or mixture of at least two high melting point fatty alcohols. When a blend or mixture of fatty alcohols is used, the melting point means the melting point of the blend or mixture.

Suitable fatty alcohols of this type have the general formula R—OH, where R is an aliphatic carbon chain. Preferably R is a saturated aliphatic carbon chain comprising from 8 to 30 carbon atoms, more preferably from 14 to 30 carbon atoms and most preferably from 16 to 22 carbon atoms.

R can contain, in addition to carbon and hydrogen atoms, ether linkages, and other groups such as amino groups.

Most preferably, the fatty alcohol has the general formula $CH_3(CH_2)_nOH$, where n is an integer from 7 to 29, preferably from 15 to 21.

Specific examples of suitable fatty alcohols are cetyl alcohol, stearyl alcohol, behenyl alcohol, and mixtures thereof. Cetyl alcohol, stearyl alcohol and mixtures thereof are particularly preferred.

Mixtures of any of the above-described fatty alcohols may also be suitable.

The level of fatty alcohol suitably ranges from 0.01 to 10%, preferably from 0.1 to 8%, more preferably from 0.2 to 7% and most preferably from 0.3 to 6% (by weight based on the total weight of the composition).

The weight ratio of cationic surfactant to fatty alcohol is suitably from 1:1 to 1:10, preferably from 1:1.5 to 1:8, optimally from 1:2 to 1:5.

An aqueous treatment composition for use in step (ii) of the method of the invention may also incorporate other optional ingredients to enhance performance and/or consumer acceptability. Suitable optional ingredients include: preservatives, colouring agents, chelating agents, antioxidants, fragrances, antimicrobials, antidandruff agents, cationic conditioning polymers, styling ingredients, sunscreens, proteins and hydrolysed proteins.

In step (i) of the method of the invention, the hair may be washed with water alone or with shampoo.

In step (ii) of the method of the invention, the washed hair is soaked in the aqueous treatment composition. Generally, any application amount of aqueous treatment composition that covers the hair to be treated suffices. Lesser amounts may be used, for example, if only a section of hair or just the hair tips are to be treated. The aqueous treatment composition is preferably uniformly delivered, for example by working it from the root end to the tip end of the hair.

Preferably, the hair is soaked in the aqueous treatment composition at a temperature from 15 to 40° C., and more preferably at a temperature from 20 to 30° C.

Preferably, the hair is soaked in the aqueous treatment composition for a period ranging from 1 to 60 minutes, more preferably from 3 to 45 minutes.

At the end of the soaking period, it is preferred that the hair is dried or allowed to dry without rinsing the aqueous treatment composition from the hair. The soaked hair may be dried naturally by exposure to air, by use of a heated hair drying appliance, by rubbing with a water-absorbent article, or by a combination of any of these methods.

The aqueous treatment composition may thus remain in contact with the hair after initial application for a period of at least 1 minute, and preferably up until the next wash, e.g. 24 to 72 hours after initial application.

The method of this invention is applied to oxidatively-treated hair.

As used herein, the term "oxidatively-treated hair" means hair which has been subjected to any treatment comprising at least one step of contacting the hair with at least one oxidizing composition. Examples of oxidative treatments for human hair are bleaching, dyeing or perming.

As used herein, the term "oxidizing composition" means a composition comprising at least one oxidizing agent suitable for use on hair, such as hydrogen peroxide, potassium, sodium or ammonium salts of perborate, percarbonate, persulfate and percarbamide, and mixtures thereof. Examples of such compositions are oxidative dye compositions and bleaching compositions.

The invention is further illustrated with reference to the following, non-limiting Examples.

EXAMPLES

In the Examples, all ingredients are expressed by weight percent of the total formulation, and as level of active ingredient. Comparative Examples (not according to the invention) are indicated by a letter; Examples according to the invention are indicated by a number.

Experiment 1

Twice-bleached dark brown European hair switches of length 25 cm and weight 2 gms, were treated as follows:

Control: After initial washing, soaked for 30 minutes in water
Example A: After initial washing, soaked for 30 minutes in a 2% aqueous solution of glycine
Example B: After initial washing, soaked for 30 minutes in a 2% aqueous solution of N-methyl glycine
Example 1: After initial washing, soaked for 30 minutes in a 2% aqueous solution of N-acetyl glycine At the end of the soaking period the switches were left to dry and clippings from a few fibres were used to measure denaturation temperature Td using DSC. The results are shown in Table 1.

TABLE 1

| Treatment | Average Td (n = 3) |
| --- | --- |
| Control (water) | 144.8 |
| Example A | 147.5 |
| Example B | 148.0 |
| Example 1 | 152.4 |

Experiment 2

Virgin dark brown European hair switches of length 25 cm and weight 2 gms, were treated as follows:
Control: After initial washing, soaked for 30 minutes in water
Example C: After initial washing, soaked for 30 minutes in a 2% aqueous solution of glycine
Example D: After initial washing, soaked for 30 minutes in a 2% aqueous solution of N-methyl glycine
Example E: After initial washing, soaked for 30 minutes in a 2% aqueous solution of N-acetyl glycine At the end of the soaking period the switches were left to dry and clippings from a few fibres were used to measure denaturation temperature Td using DSC. The results are shown in Table 2:

TABLE 2

| Treatment | Average Td (n = 3) |
| --- | --- |
| Control (water) | 148.8 |
| Example C | 147.7 |
| Example D | 148.0 |
| Example E | 151.9 |

It can be seen from the results that treatment of bleached switches with N-acetyl glycine according to the method of the invention (Example 1) provides a substantial and significant increase in Td of the treated fibres, when compared to treatment with glycine or N-methyl glycine (Examples A and B respectively). Furthermore, the effect of the N-acetyl glycine is selective towards the bleached switches, as can be seen from a comparison with Examples C to E. In particular, while the Td of Example E is 3.1° above its control, the Td of Example 1 is 7.6° above its control. This shows that the method of the invention has the potential to repair hair fibres which have been damaged by oxidative treatments such as bleaching.

The enhanced fibre strengthening provided by the method of the invention may also help to prevent or reduce further fibre damage in the future, whether caused by oxidative treatment or otherwise.

Example 2

The following formulation illustrates an aqueous treatment composition for use in the method of the invention.

| Ingredient | % activity | % w/w raw material |
| --- | --- | --- |
| Behentrimonium chloride | 70 | 1.1429 |
| Cetearyl alcohol | 100 | 3.0 |
| Perfume | 100 | 0.60 |
| Preservative | 100 | 0.2 |
| Dimethicone emulsion | 70 | 1.429 |
| N-acetyl glycine | 100 | 2.0 |
| Water, minors | 100 | To 100% |

The invention claimed is:
1. A method of strengthening the fibres of oxidatively-treated hair, the method comprising the sequential steps of:
   (i) washing the oxidatively-treated hair;
   (ii) soaking the washed hair in an aqueous treatment composition, and
   (iii) drying the soaked hair;
   wherein the aqueous treatment composition comprises at least 1% N-acetyl glycine by weight based on the total weight of the composition.
2. The method of claim 1, wherein the N-acetyl glycine is used in the free acid form, and at a level ranging from 1.5 to 2.5% by weight based on the total weight of the composition.
3. The method of claim 1 wherein, the hair is soaked in the aqueous treatment composition at a temperature from 15 to 40° C.
4. The method of claim 1 wherein, the hair is soaked in the aqueous treatment composition for a period ranging from 3 to 45 minutes.
5. The method of claim 1 wherein at the end of the soaking period, the hair is dried or allowed to dry without rinsing the aqueous treatment composition from the hair.

* * * * *